(12) United States Patent
Craig

(10) Patent No.: US 6,626,917 B1
(45) Date of Patent: Sep. 30, 2003

(54) HELICAL SUTURE INSTRUMENT

(76) Inventor: H. Randall Craig, 3200 N. Dobson Rd. #F, Chandler, AZ (US) 85224

(*) Notice: Subject to any disclaimer, the term of this patent is extended or adjusted under 35 U.S.C. 154(b) by 414 days.

(21) Appl. No.: 09/980,556

(22) PCT Filed: Oct. 26, 2000

(86) PCT No.: PCT/US00/29508
§ 371 (c)(1),
(2), (4) Date: Oct. 31, 2001

(87) PCT Pub. No.: WO01/30245
PCT Pub. Date: May 3, 2001

(51) Int. Cl.[7] ............................................ A61B 17/04
(52) U.S. Cl. ...................................... 606/144; 606/148
(58) Field of Search ..................... 606/139, 146–148, 606/222, 223, 232, 61

(56) References Cited

U.S. PATENT DOCUMENTS

| | | | |
|---|---|---|---|
| 5,018,530 A | 5/1991 | Rank et al. | |
| 5,330,503 A | 7/1994 | Yoon | |
| 5,356,424 A | 10/1994 | Buzerak et al. | |
| 5,368,595 A | 11/1994 | Lewis | |
| 5,405,376 A | 4/1995 | Mulier et al. | |
| 5,423,836 A | 6/1995 | Brown | |
| 5,499,990 A | 3/1996 | Schülken et al. | |
| 5,545,148 A | 8/1996 | Wurster | |
| 5,562,685 A | 10/1996 | Mollenauer et al. | |
| 5,582,616 A | 12/1996 | Bolduc et al. | |
| 5,662,683 A | 9/1997 | Kay | |
| 5,695,462 A | 12/1997 | Sutcu et al. | |
| 5,709,692 A | 1/1998 | Mollenauer et al. | |
| 5,820,631 A | 10/1998 | Nobles | |
| 5,947,983 A | 9/1999 | Solar et al. | |
| 6,315,784 B1 * | 11/2001 | Djurovic | 606/146 |

* cited by examiner

*Primary Examiner*—Julian W. Woo

(57) ABSTRACT

A helical suturing instrument is provided which either pushes or pulls a suture along a helical needle tract. The instrument has one or more helical needle portions, each with a suture retaining component.

62 Claims, 9 Drawing Sheets

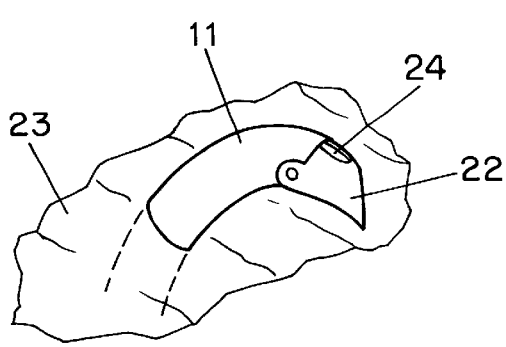
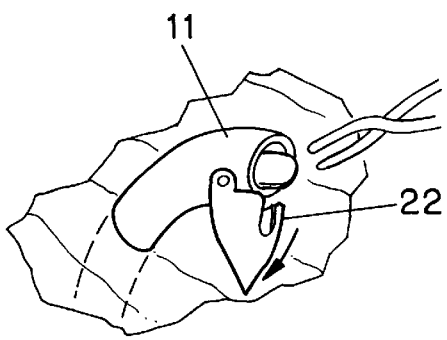
FIG. 4A      FIG. 4B
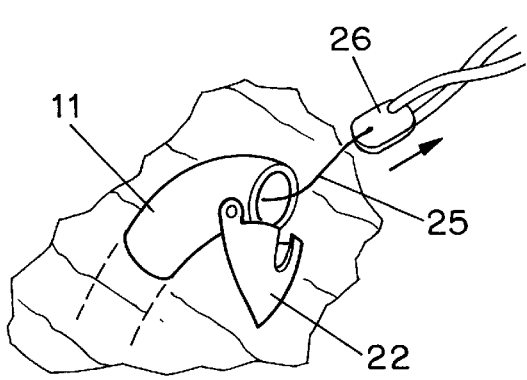
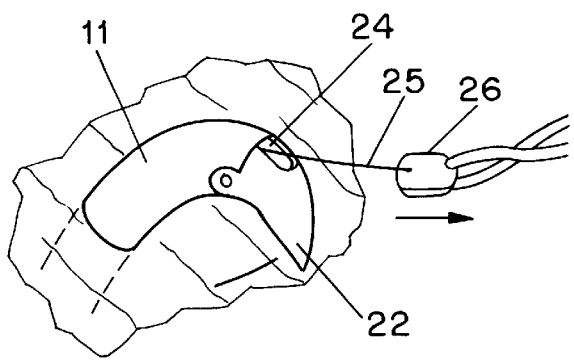
FIG. 4C      FIG. 4D
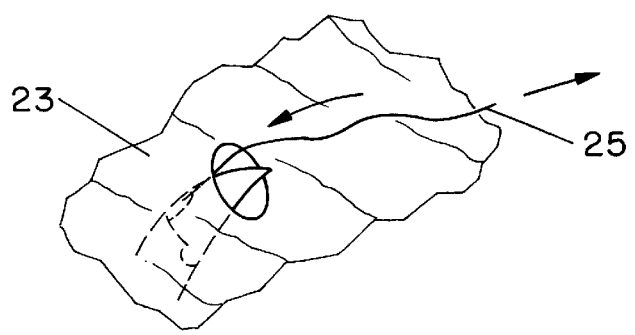
FIG. 4E

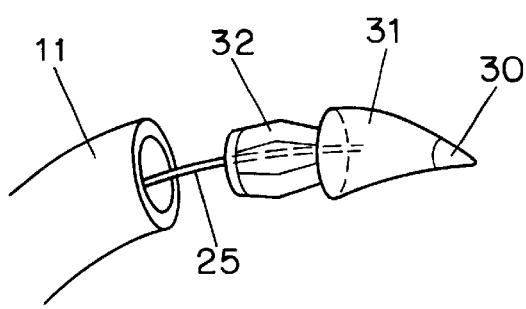
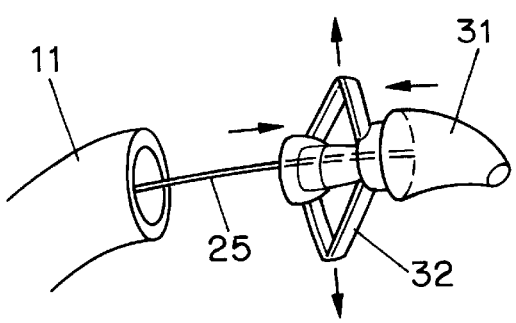
FIG. 7A   FIG. 7B
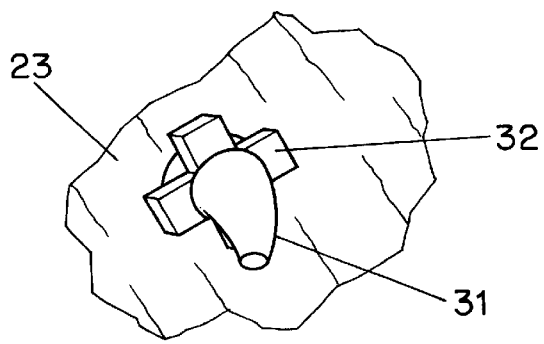
FIG. 7C
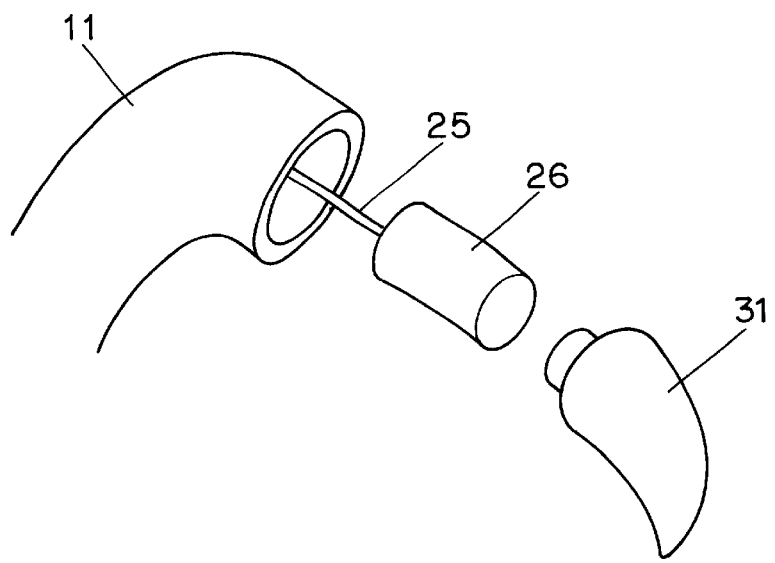
FIG. 8

HELICAL SUTURE INSTRUMENT

BACKGROUND OF THE INVENTION

This applicaton claims priority from U.S. Provisional Application No. 60/161,584 filed Oct. 26, 1999, which is incorporated herein by reference.

The present invention relates to a suturing instrument. The purpose of suturing is to connect two surfaces or layers of substrate by means of a thread, line, cable, or wire which is repeatedly inserted and withdrawn alternately in each layer or surface. This is done in order to connect at least two layers or surfaces in direct opposition to each other in order to 1) fuse the layers or surfaces into one unit, 2) close a surgical incision or wounded biological tissue, or 3) produce a watertight or airtight vessel.

There are two primary applications for suturing. The first is medical and biological, for surgical repairing or closing wounds and incisions in living tissue. The second is commercial and industrial applications for connecting or sewing together fabrics or sheets of various materials such as textiles, clothing, sails, sport equipment, or binding of paper products. The suture material must be a long flexible substance with enough tensile strength to hold layers together, and includes string, wire, cable, protein (hair), natural fibers, or a synthetic polymer such as nylon or vicryl. The suture material can be permanent, temporary (to hold substrates together for a short duration or until another connecting method is applied such as glue or welding), or absorbable. Absorbable suture material is typically used for biological applications, with the suture eventually broken down and dissolved in living tissue after a wound has healed.

The material being sutured is the substrate, and usually consists of opposing surfaces to be brought together, typically in direct contact. These opposing surfaces can be composed of one substance, or different substances. Commercial substrates usually consist of layers of materials such as rubber, paper, cloth, or other textiles. Medical and biological substrates are usually composed of wounds or incisions in skin, muscle, fascia, or internal organs.

SUTURING METHODS

Ancient suture methods are still the most common type, typically requiring basic needle and suture materials. Suture alone is too flexible to penetrate substrates, so it is typically attached to a rigid penetration device with a sharpened end, such as a needle, spike, lance, or harpoon. Usually, the needle is alternately inserted into one surface of the substrate by penetration, and pulled out from a nearby site. This is repeated on the opposite surface of the substrate, and when the suture is pulled taut, the two surfaces are brought together into immediate proximity or contact. The degree of tension applied to the suture determines how tightly the substrates are held together. Placing a single suture through two or more substrate layers or surfaces completes a single "suture cycle" with the result being a "stitch".

In general, multiple adjacent sutures were placed in a linear fashion by repeating the basic suture cycle, typically resulting in a line of adjacent, evenly spaced stitches. The result is a "suture line".

Several suturing devices have been developed to operate suture cycles. Manual devices are composed of needle and thread which are placed by simple hand dexterity. Clamps and needle drivers have been developed to allow manual driving of needles through resistant substrates that would be difficult or impossible to penetrate using hand dexterity. Finally, automated sewing machines typically use two or more threads and an automated needle penetration and entanglement device to rapidly and automatically develop a suture line.

Current suturing technology will be illustrated by medical suturing; the same basic principles apply to commercial and industrial suturing. This technology is designed to join tissue surfaces to close wounds or incisions, or stop bleeding. Less commonly, medical suturing is used to place a line into a tissue plane for retraction to gain greater access to a surgical field. The following medical suture types are routinely used:

Interrupted sutures are composed of single separated stitches, which are typically placed at even intervals along an incision.

Continuous sutures are achieved by placement of a single stitch at one end of an incision, and then repeating the suturing cycle sequentially along the incision to the opposite end. This is also called a "running stitch".

Continuous and locked sutures are the same as continuous sutures, but with the needle and suture material occasionally passed under the previous stitch before continuing to the next suture cycle.

Purse string sutures are used primarily to close circular or cylindrical defects. A knot is tied at one end of a suture, and using a curved needle the other end of the suture is passed in a circular manner around the bottom of the incision towards the starting point, then continued in an upward spiral toward the top of the incision. Once the surface is reached, the suture is pulled tight which closes the circular defect in a "purse-string" type manner.

Figure eight sutures consists of two suture cycles crossed over each other in an "X" pattern.

The current suture cycle technique used for nearly all surgical applications consists of several steps:

1. Obtain suture and attached needle, usually from a sterile package.
2. Clamp a needle driver onto the midportion of the needle.
3. Manually use the needle driver to push the needle into the tissue surface on one side of the incision.
4. Push and/or rotate the needle through the tissue with the needle driver until the tip of the needle emerges from the tissue surface nearby.
5. Unclamp the needle driver from the midpoint of the needle, move the needle driver to the emerging needle tip, and reclamp the needle tip with the needle driver.
6. Pull and/or rotate the needle from the tissue surface with the driver, then continue to pull until the entire length of the needle emerges from the tissue. This leaves the suture in the tissue along the needle track.
7. Pull the suture through a short distance.
8. Regrasp the needle at the midpoint with the needle driver.
9. Push the needle through the tissue surface on the opposite side of the incision, push and/or rotate the needle through the site until the tip of the needle emerges from the tissue surface nearby.
10. Unclamp the needle driver from the needle midpoint, move it to the needle tip, and reclamp the needle tip with the driver. Pull and/or rotate the needle from the tissue surface with the needle driver until the entire length of needle emerges from the tissue.
11. Pull the suture through the opposite tissue surface.

These steps complete the basic suture cycle, and all surgical suturing techniques are built from the components of this cycle. Note that the needle handling instrument (needle driver or clamp) must be unclamped from the needle, then reclamped onto the needle multiple times to complete a single stitch cycle. This is currently the primary method of placement of sutures used worldwide, with the disadvantages of being labor intensive and tedious, requiring multiple repetitions of the stitch cycle progressing down the length of the incision.

After an interrupted suture is placed, the suture is pulled taut and tied (usually with square knots). If a continuous suture is to be placed, multiple repeats of the basic cycle are done until the entire length of the incision is covered. Then the suture is pulled taut and tied. Each suture cycle is called a "throw" and each throw results in placement of one stitch. If continuous and locked sutures are to be placed, the free suture is passed under the previous loop formed by the previous stitch before the next suture cycle is initiated. A figure eight suture is essentially two "crossed over" throws.

Suture cycles are tedious multistep procedures which are time intensive. They require relatively intensive labor and result in a relatively slow closure of incisions or wounds. A more efficient method of placing sutures would save time and labor, and would reduce the total operating room time and anesthesia time, allowing scheduling of more cases in a fixed period of time such as an operating room (O.R.) shift.

Several suturing devices involving helical-shaped needles are known. U.S. Pat. Nos. 5,356,424 (Buzerak et al.) and U.S. Pat. No. 5,562,685 (Mollenauer et al.) disclose laparoscopic suturing devices with a helically-wound front-end portion with a needle point. Some of the disadvantages of these devices include the necessity of using multiple cannulas for introducing additional surgical instruments such as forceps, cutting instruments and light sources. In some embodiments of the Buzerak et al. device the helical needle is removed from its handle in order to tie the suture. In another embodiment, the helical needle is hollow and contains suture material, but there is nothing to keep the suture material secure at the needle tip while the needle is rotated into the tissue.

U.S. Pat. No. 5,330,503 (Yoon) discloses spiral and helical-shaped absorbable suture needles. The needles have barbs and a locking device to prevent their movement after they are placed in the tissue. The needles are designed to be used without suture material.

U.S. Pat. No. 5,545,148 (Wurster) discloses an endoscopic suturing device which uses a separate helical-shaped needle with a suture attached to the blunt end. The device utilizes two rods to manipulate the needle.

SUMMARY OF THE INVENTION

A first embodiment of the invention is a suturing instrument comprising first and second members. The first member comprises a first helical portion and a second straight portion, the helical portion having a configuration including at least one complete revolution of a helix. The first member has a means for attaching a suture. The helix has a central axis and a sharpened tip.

The second member comprises a straight hollow member having an interior lumen extending from a first open end to a second open end. The straight portion of the first member is attached to the first end of the second member such that the second member is disposed within the helical portion of the first member along the central axis of the helix. The second end of the second member extends toward the sharpened tip of the first member.

A second embodiment of the suturing instrument comprises first and second members and a connecting member. The first and second members each have a first helical portion and a second straight portion. The helical portions each have a configuration including at least one complete revolution of a helix. The helices each have a central axis and a sharpened tip.

The first and second members each comprise a means for attaching a suture. The straight portions of the first and second members are attached to the connecting member such that the first and second members are disposed side by side, with parallel central axes.

A third embodiment of the suturing device comprises at least a first member and a handle, the member having a first helical portion and a second straight portion. The helical portion has a configuration including at least one complete revolution of a helix. The helix has a central axis and a sharpened tip. The member has a means for attaching a suture. The handle has first and second sections connected by a universal joint. The handle is attached to the straight portion of the member.

A fourth embodiment of the suturing device comprises first and second members and a means for simultaneously rotating the first and second members. The first and second members each have a first helical portion and a second straight portion, the helical portions having a configuration including at least one complete revolution of a helix. Each helix has a central axis and a sharpened tip. The first and second members each have a means for attaching a suture. The straight portions of the first and second members are attached to the means for simultaneously rotating the first and second members.

A fifth embodiment of the invention is a method for suturing a tissue comprising introducing a suturing instrument into the tissue, rotating the instrument in a first direction into the tissue, creating a path for the suture, rotating the instrument in a second direction out of the tissue, wherein the suture is deposited along the path.

A sixth embodiment of the invention is a method for loading a suture into a helical suturing instrument. The method comprises the steps of attaching a length of suture material to an end fitting, placing the end fitting with attached suture into one end of the hollow member, and moving the end fitting through the hollow member from one end to the other end. The end fitting deposits the suture material along the length of the hollow member.

BRIEF DESCRIPTION OF THE DRAWINGS

FIGS. 4A–4E show the steps of using a hollow helical member with a hinged tip and internal suture.

FIGS. 7A–7C show a hollow helical member with a freely detachable sharpened tip and break-away sharp tip, which forms an expandable anchor.

FIG. 8 shows a hollow helical member with a freely detachable sharpened tip and an end fitting attached to a suture.

DETAILED DESCRIPTION OF THE INVENTION

The present invention, a helical suturing instrument, results in the placement of a continuous suture with substantially increased efficiency. Less time and labor are required with the present instrument because multiple throws of the suture can be rapidly and easily performed.

The method of the instant invention involves rotating a rigid helix with a sharp tip longitudinally down an incision with the sharp tip of the helix alternately entering and exiting the opposite surfaces of tissue with each rotation.

The instant invention involves a two-step procedure: 1) advance a rigid helix through the incision tissue by rotation, and 2) withdraw the helix out of the tissue by counter-rotation. The suture material is carried through the helical track by being temporarily attached to the front needle tip end of the rigid helix. After the rigid helix is withdrawn by counter-rotation, the suture is left behind in the helical needle track and it is then pulled taut and tied to close the incision.

The suture material can either be "pushed" or "pulled" by the tip of the rigid helix needle tip. This invention can, therefore, be configured as one of two basic types.

The type I device "pushes" the suture material through the substrate. The simplest version of a type I device is a rigid helical needle with the end of the suture attached to the tip. The helical needle is rotated into the incision tissue longitudinally from one end to the other, the needle tip repetitively entering one side and exiting the other side of the incision, dragging the suture along. Once the end of the incision has been reached by the helical needle tip, further rotation of the needle is stopped with the needle tip exposed in the upper portion of the incision. With the needle tip exposed, the end of the suture is detached from the needle and held in place. The helical needle is then counter-rotated, backtracking through the tissue until it has been withdrawn, leaving the suture in place along the helical needle tract. The suture is then drawn taut and knotted to close the incision. The completed suture is a continuous suture or "running stitch", achieved using a single stitch cycle instead of the multiple individual stitch cycles required in conventional suturing with semicircular needles and needle holders.

The type II device "pulls" the suture material back through the substrate. The simplest version of a type II device is a rigid helical needle with no suture initially attached. The helical needle is rotated through the incision tissue longitudinally from one end to the other. Then with the needle tip exposed at the far end of the incision, the end of the suture is attached to the needle tip. The helical needle is then counter-rotated, backtracking through the tissue until it has been withdrawn, pulling the suture along the needle track. The suture is then detached from the needle tip, drawn taut and tied to close the incision.

Figure 1:
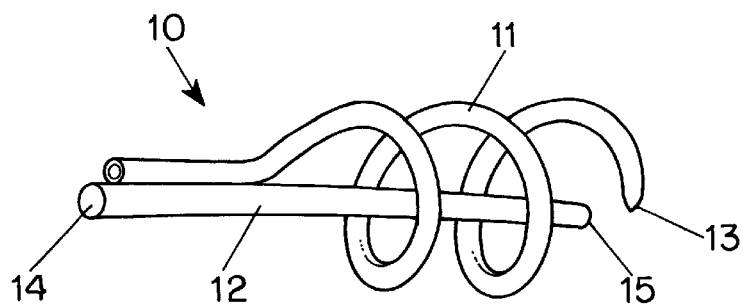
FIG. 1 shows an embodiment of the invention with one helical member and one straight member.
Figure 12:
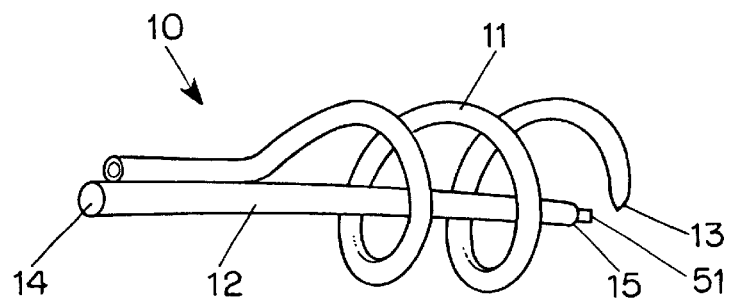
FIG. 12 shows a light source.
Figure 13:
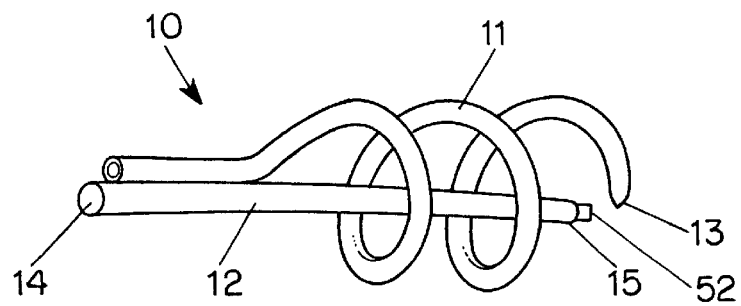
FIG. 13 shows an observation tool.

A first embodiment of the invention is a suturing instrument 10 comprising first 11 and second 12 members (FIG. 1). The first member has a helical portion and a straight portion. The helical portion is configured to include at least one complete revolution of a helix, and has a sharpened tip 13. The helix has a central axis and comprises a means for attaching a suture. The second member is hollow, with an interior lumen extending from a first open end 14 to a second open end 15. The straight portion of the first member is attached to the first end of the second member such that the second member is disposed within the helical portion of the first member along the central axis of the helix in the geometric center of the helix coils. The second end 15 of the second member extends towards the sharpened tip 13 of the first member. The second hollow member functions as a guide to keep the helix rotational advance aligned longitudinally down the incision and to allow proper placement and depth of the helix coils. The second hollow member may also function as a holding channel for the suture, especially for the "pushing" type I device. The second hollow member can also function as a container for suture material to be removed and inserted into a catch or snag portion of a "pushing" type II device. One of the advantages of the second hollow member 12 is as a support for various accessories for the helical suturing device, including an illumination light (shown at 51 in FIG. 12) or fiber optic viewing channel (shown at 52 in FIG. 13). The length of the second hollow member can be longer, shorter, or the same length as the helical portion of the first member, depending on the assigned function.

Figure 11:
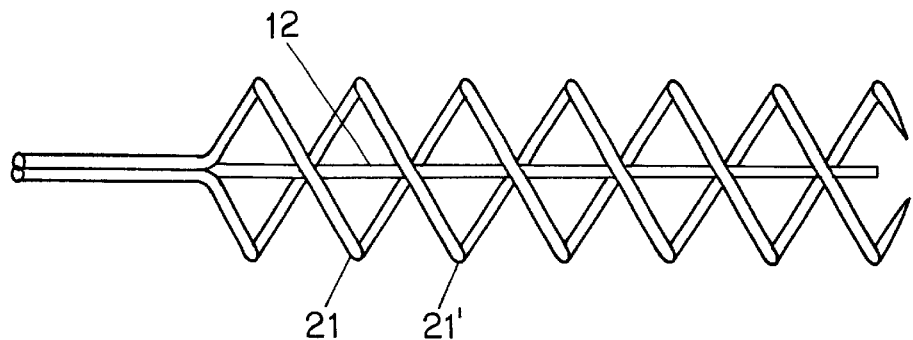
FIG. 11 shows first, second, and third members.

This embodiment may additionally comprise a third member 50 (FIG. 11), identical to the first member 11, with a helical portion and a straight portion. The straight portions of the first and third members are attached to the first end of the second member such that the second member is disposed within the helical portions of the first and third members along the central axis of the helices. The second end of the second member extends towards the sharpened tips of the first and third members. This embodiment allows for placement of two intertwined continuous sutures using two helical tracts. The two helical portions may have identical radii, diameters, number of turns, and pitches, but may be offset aligned along the same central axis. Alternatively, the first and third members may have helices with different diameters, radii, number of turns and pitches.

Figure 14:
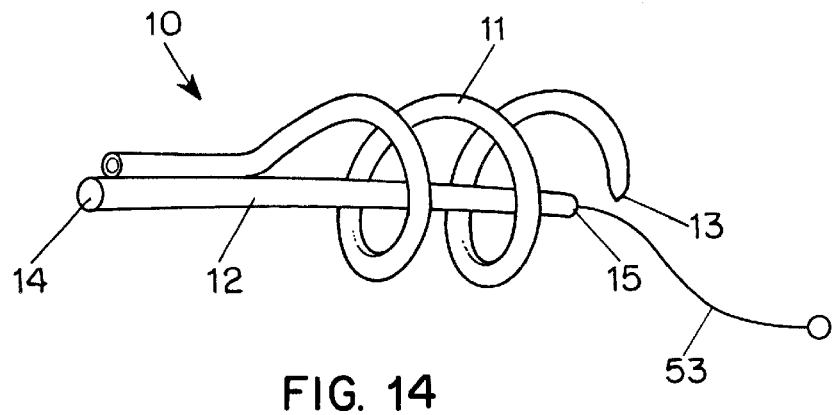
FIG. 14 shows a tether line.

A further embodiment comprises a tether line (53 in FIG. 14) attached to the second end of the second member 12. The tether line is used to provide fine adjustment to the position of the suturing instrument in the incision. The tether line is especially useful for long suturing instruments with many helical rotations, because fine position adjustment may not be able to be achieved with movement of the straight portion of the first member. One can use the tether line to guide and make position adjustments as the instrument is rotated into the tissue. The tether line is also useful for inserting the instrument into especially thick or hard tissues. The tether line may be made of wire, thread, suture material, or any other material which can be attached to the second member and provide adequate strength for manipulating the instrument. The tether line may include a flattened end or tab for ease of grasping the line.

Figure 15:
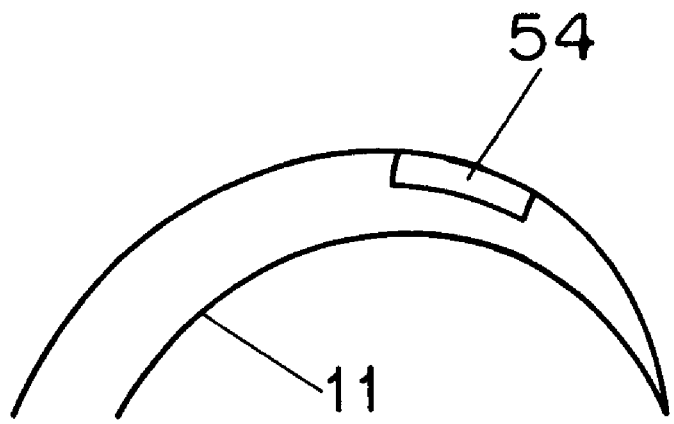
FIG. 15 shows a gate.

The first and third members may be solid or hollow. When the first and/or third members are solid, the means for attaching a suture near the tip of each helix may be a catch, hook or notch in the outer surface of the member near the tip, a hole through the member near the tip, or any other means of removably attaching a suture to the member. After rotation of the suturing instrument through a tissue, the suture material is then inserted into the catch or notch on the exposed helix tip. Counter-rotation withdrawal of the instrument results in dragging the suture behind the helical portion of the member into the helical tract. Small inward-pointing teeth inside the catch or notch may be added to better secure the suture and minimize slipping. A notch may comprise a gradually narrowing channel such that the suture is secured by friction at the narrow end of the channel. Alternative means for attaching a suture to the helix tip include an opening with a spring-mounted latch or gate (54 in FIG. 15). A groove cut along the interior edge of the helical portion throughout its length may also function as the means for attaching a suture to a solid member. The groove is designed to hold the suture against the interior curve of the helical portion as it rotates through tissue.

For the embodiment having first and third solid members, the second straight member may be used to transport a suture. The second hollow member contains a single length of suture with two looped ends, the looped ends extending from the second end of the straight member. In use, the instrument in rotated into a tissue, the looped ends are attached to the two catch portions of the helix tips, and after counter-rotation withdrawal of the instrument, the two free ends are then tied together for closure. In an alternate embodiment, once the instrument is rotated into place, one end of the suture which contains a small loop is a attached to the catch portion of one helix tip.

When the instrument is counter-rotated one-half turn, the other helix tip is now positioned to receive the other end of the suture. Once this is attached, the instrument is counter-rotated and withdrawn, pulling the two ends of the suture along the helical tracts. During this process, the free midportion of the suture is slowly pulled out of the straight hollow member until its length is entirety consumed. At this point, pulling both ends of the suture results in closure of the incision.

Figure 2A:
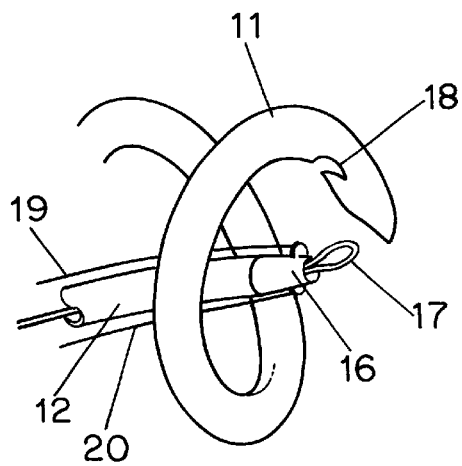
FIGS. 2A–2C show an embodiment of FIG. 1 with a hinged straight member for depositing a suture loop on a catch on the helix.
Figure 2B:
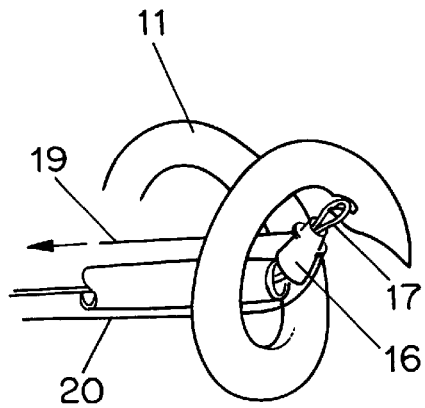
Figure 2C:
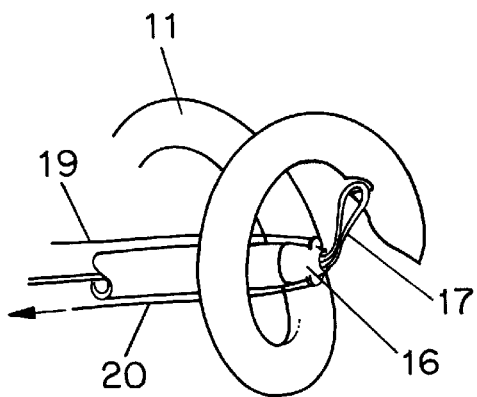

A hinged tip 16 on the straight hollow member 12 provides a means for storing and attaching a suture to the end of a solid first and/or third member 11 (FIGS. 2A–2C). An opening in the hinged tip allows the loop end 17 of a suture to be attached to a catch 18 on the member. After the suturing instrument is rotated into a tissue, the hinged tip 16 is opened and the suture loop 17 is placed over the catch 18. The hinged tip is then closed and the suturing instrument is counter-rotated out of the tissue. In a particular embodiment, the straight member 12 comprises an ipsilateral wire 19 and a contralateral wire 20, both attached to the hinged tip (FIG. 2A). The hinged tip is opened by pulling the ipsilateral wire 19 (FIG. 2B). When the contralateral wire 20 is then pulled, the hinged tip closes, resulting in placement of the suture loop 17 into the catch 18 on the member (FIG. 2C). The suturing instrument is then counter-rotated and withdrawn, pulling the suture behind it through the helix tract.

The suture is slowly extracted from the straight hollow member during this process.

Figure 16:
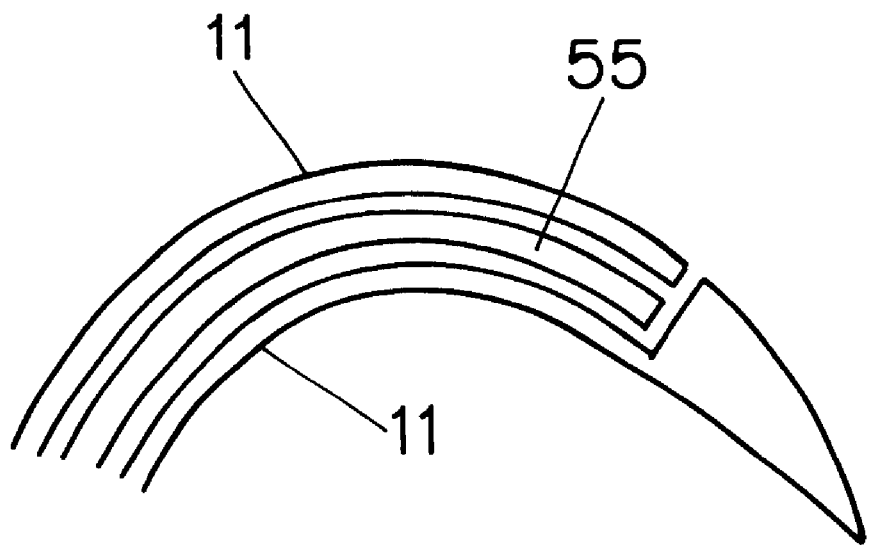
FIG. 16 shows an internal push rod.

When the first and/or third members are hollow, they comprise an interior lumen extending from a first open end to a second open end at the tip of the helical portion. The means for attaching a suture to a hollow member include internal spring-loaded catches, a spring-loaded sliding plug inside hollow tip operated by a pull-wire threaded through the hollow member, or a helical push rod (55 in FIG. 16) which fits inside the lumen of the hollow member. In use, once the instrument is inserted into a tissue, a suture is attached to the helix tip by inserting the suture into the opening in the member and applying steady pressure with the push rod against the suture.

In another embodiment utilizing a hollow member with an opening behind the tip, a hook is disposed inside the member just inside the opening. The hook is connected to a pulling means, such as a wire or string which travels the length of the member to the outside. This type of device is used with a suture having a loop at one end. In use, the loop end of the suture is placed over the hook, and the pulling means is pulled, causing the hook and attached suture to travel into the hollow member. This type of suture attachment can be used with either the "pushing" (type I) or "pulling" (type II) helical suturing instruments. For the "pushing" type I instrument, the suture is attached to the hook, the instrument is rotated into the tissue, the suture is disengaged from the hook and held in place, and the instrument is counter-rotated out of the tissue For the "pulling" type II instrument, the suturing instrument is rotated into the tissue, the suture is attached to the hook, the instrument is counter-rotated out of the tissue, and the suture is disengaged from the hook.

An embodiment for a means of attaching a suture to a type I (pushing) device with a hollow member is a detachable tip. The suture is threaded through the hollow member and connected to the detachable tip. After the suturing instrument is rotated through the substrate, the exposed tip is physically removed from the rest of the member. The tip with its attached suture is then held in place while the instrument is withdrawn by counter-rotation. The hollow member slides "out from under" the suture, leaving the suture behind along the helical tract.

The interior lumen of the first hollow member may exit the helical member in a variety of locations. The simplest is a flush opening into the end of the handle of the device. The interior part of the helix can be extended beyond the handle at its center axis, or can be bent so that the interior lumen emerges from the side of the handle. The side of the straight portion of the member can also contain an opening to the interior lumen, or the helix itself can be wrapped around a center cylindrical handle and shaft with the interior lumen consisting of the exposed end of the helix.

Any other suitable means of attaching a suture to the helix tip such that the suture remains secured during rotation and/or counter-rotation of the suturing instrument into and out of a tissue, but allows for removal of the suture for tightening and knotting, are encompassed by the invention.

A further embodiment is a hybrid Type I and Type II instrument comprising a first solid member, a third hollow member, and a straight hollow second member with a hinged tip. A hook on the end of the straight member hinged tip is manipulated so that it extracts the end of the free suture being carried by the third hollow member, then transfers it to the catch portion of the tip of the solid first member. After this is done, the instrument is then counter-rotated and withdrawn, with the first solid member dragging the suture behind it along its tract, while the third hollow member allows the same suture to be withdrawn in the opposite direction to provide the increasing length required for this process. Once the instrument is completely withdrawn from the incision, the two ends of the suture can then be pulled tight in order to close the incision.

In another embodiment, the first and/or third member is hollow, contains a suture, and the sharpened tip is hinged to allow access to the interior suture without complete detachment of the tip (FIGS. 4A–4E). FIG. 4A shows the member 11 with hinged tip 22 protruding from a tissue 23. A slot 24 in the hinged tip 22 allows the suture 25 to move freely out of the member 11 once the hinged tip 22 is replaced. FIGS. 4B and 4C show opening the hinged tip 22 and removing a length of suture 25. The suture 25 is attached to an end fitting 26 such as a tab to make it easier to grip and hold onto with a surgical instrument such. Once a length of the suture 25 and end fitting 26 has been removed from the member 11, the hinged tip 22 is closed (FIG. 4D), the suture is held in place and the member is withdrawn from the tissue (FIG. 4E).

The end fitting may be a flattened tab for grasping the suture, or may have a structure such that it functions as an anchor to secure the suture. The end fitting may also be a plug which holds the attached suture securely inside a hollow member.

The forces applied to the tip of the advancing helical instrument consist primarily of two components, the first is directed against the tip in the direction opposite of advance, the second component of force tends to push the tip of the helix outward away from the axis of the helix. Because of this second force, a hinged tip must either have the hinge itself placed on the inside edge of the helix, or have a locking mechanism if the hinge is on the outside edge of the helix, to prevent the hinged tip from opening during rotation of the helical instrument into a tissue.

Figure 5:
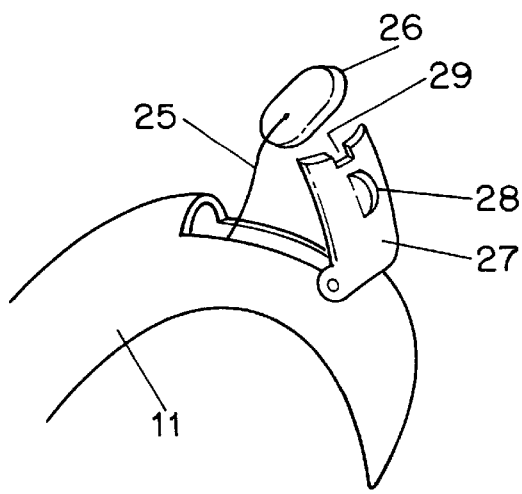
FIG. 5 shows a hollow helical member with a hinged opening on the outer curve of the helix.

An alternate embodiment of a hinged opening in the hollow helical instrument is shown in FIG. 5. In this embodiment, a hinged door 27 is disposed on the outer edge of the helical portion of the member 11. The hinged door 27 comprises a handle 28 for opening the door, a slot 29 to allow the suture 25 to move freely out of the helical instrument once the hinged door 27 is replaced, and a latch mechanism to prevent unintentional opening during the counter-rotation and withdrawal step.

In one embodiment, the helical suturing instrument comprises a hollow helical member with a detachable sharpened tip. It its basic form, the sharpened tip is freely detachable from the helical member and is attached to a suture. In order to keep the freely detachable tip in place on the helical member during rotation into a tissue, the instrument further comprises a means for holding the suture. The means for holding the suture puts tension on the suture which holds the detachable tip in place. Once the instrument is rotated into a tissue, the suture is released from the means for holding the suture, and the tip with attached suture is removed from the helical member and held in place while the instrument is counter-rotated out of the tissue. The sharpened tip may then be removed from the suture so that the suture may be knotted. In alternative embodiments, the detachable sharpened tip is modified to create an anchor for the suture. In these embodiments, the suture is not removed from the tip, and the anchor takes the place of a knot in the suture.

A break-away sharp tip may be used when the detachable sharpened tip is to be modified to form an anchor. A scored notch near the end of the tip provides a means for breaking off just the sharp end, leaving the remaining detachable portion to form an anchor. Removing the sharp tip prevents irritation or injury which would be caused by the sharp tip rubbing against adjacent tissue during the healing process.

Figure 6A:
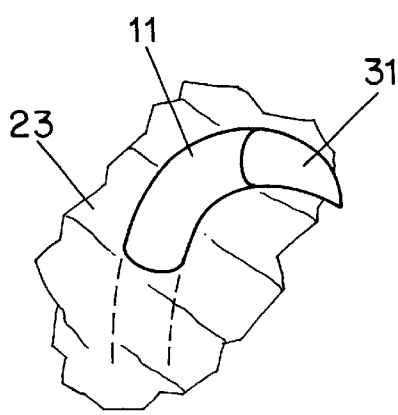
FIGS. 6A–6D show a hollow helical member with a freely detachable sharpened tip and break-away sharp tip, which forms a toggle anchor.
Figure 6B:
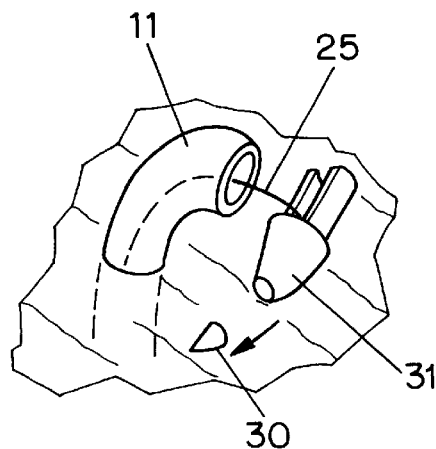
Figure 6C:
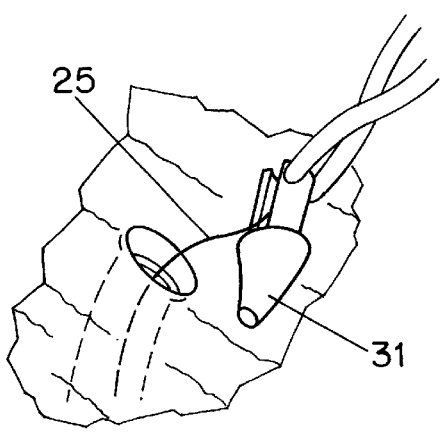
Figure 6D:
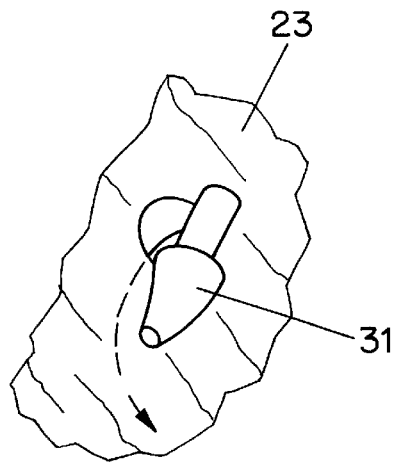

FIGS. 6A–6D show a particular embodiment of the break-away sharp tip 30 in which the detachable tip 31 is modified to create a toggle anchor. FIG. 6A shows the helical member 11 of the suturing instrument exiting a tissue 23. The detachable sharpened tip 31 is removed from the helical member 11 and the break-away sharp tip 30 is removed (FIG. 6B). The remaining portion of the sharpened tip is held in place while the helical member is withdrawn from the tissue (FIG. 6C). In this embodiment, the sharpened tip is modified such that the suture can be moved perpendicular to the detached sharpened tip. When the suture is pulled tight, the detached sharpened tip forms a toggle anchor (FIG. 6D).

An alternate anchor embodiment is shown in FIGS. 7A–7C. The detachable sharpened tip 31 comprises a break-away sharp tip 30 and an expandable base section 32. In use, the sharpened tip 31 is detached from the helical member 11 (FIG. 7A), the break-away sharp tip 30 is removed, and the base section 32 is expanded (FIG. 7B). When the suturing instrument is withdrawn and the suture is pulled tight, the expanded base creates an anchor for the suture (FIG. 7C).

Instead of having the detachable sharpened tip modified to create an anchor, an end fitting 26 may be used. FIG. 8 shows the basic form of an end fitting 26 attached to a suture 25. The end fitting 26 with attached suture 25 is positioned just inside the detachable sharpened tip 31. In use, once the instrument is rotated into a tissue, the sharpened tip 31 is detached and the end fitting 26 with attached suture 25 is removed from the helical member 11 and held in place while the instrument is withdrawn from the tissue. The end fitting may then be removed from the suture to knot the suture, or the end fitting may be modified to create an anchor. Examples of end fittings which form anchors include a toggle anchor system, expanding devices, an inflatable balloon, or a loop and button system.

The detachable sharpened tip may be freely detachable, in which case a means for holding the freely detachable tip in place during insertion of the suturing instrument is required. The freely detachable tip may be removably attached to the end fitting, in which case a means for holding the suture is needed to maintain tension on the suture, which keeps the detachable tip in place. Alternatively, the detachable sharpened tip may be removably attached to the helical member. The detachable sharpened tip may be threaded either externally or internally to match corresponding threading on the helical member. In this embodiment, the sharpened tip is screwed off after the instrument is inserted into the tissue, to retrieve the end fitting and suture. The helical member may be scored behind the sharpened tip such that in use, the sharpened tip is broken off to allow access to the end fitting and suture.

An embodiment utilizing an end fitting without a detachable tip on the helical member involves an aperture with a cover in the inner curve of the helix near the sharpened tip. The cover may be a rupturable membrane. A length of suture is attached to an end fitting positioned inside the hollow helical member such that the end fitting is disposed inside the aperture and the length of suture extends through the hollow helical member. The membrane may be ruptured by external force, for example by using a surgical instrument, or may be ruptured by internal force, for example by liquid or gas pressure. In a specific embodiment, aperture cover is a removable cover attached to the end fitting. In use, gas or liquid is forced through the hollow helical member, which forces the cover and attached end fitting out of the helical member. This configuration allows easy recovery of the end fitting, avoids the requirement for meticulous extraction of the end fitting from the interior of the hollow helix.

Figure 3A:
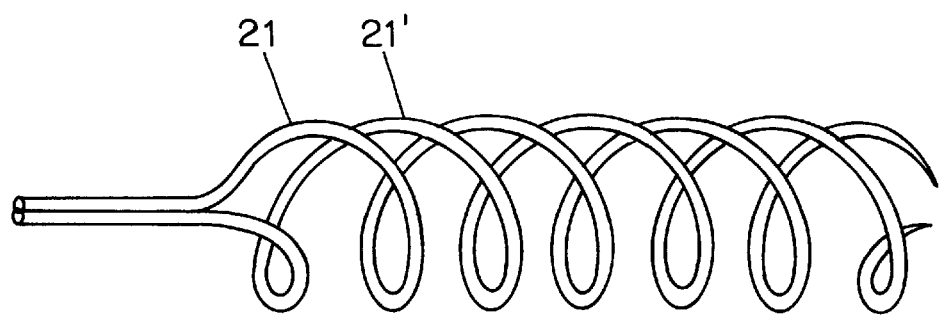
FIGS. 3A–3C show a double helical member suturing instrument.
Figure 3B:
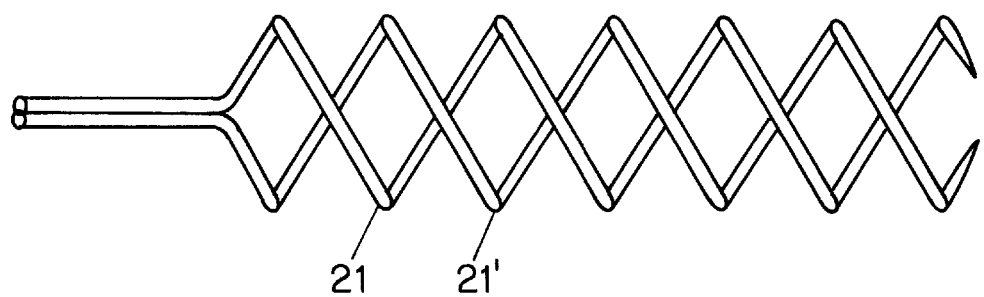
Figure 3C:
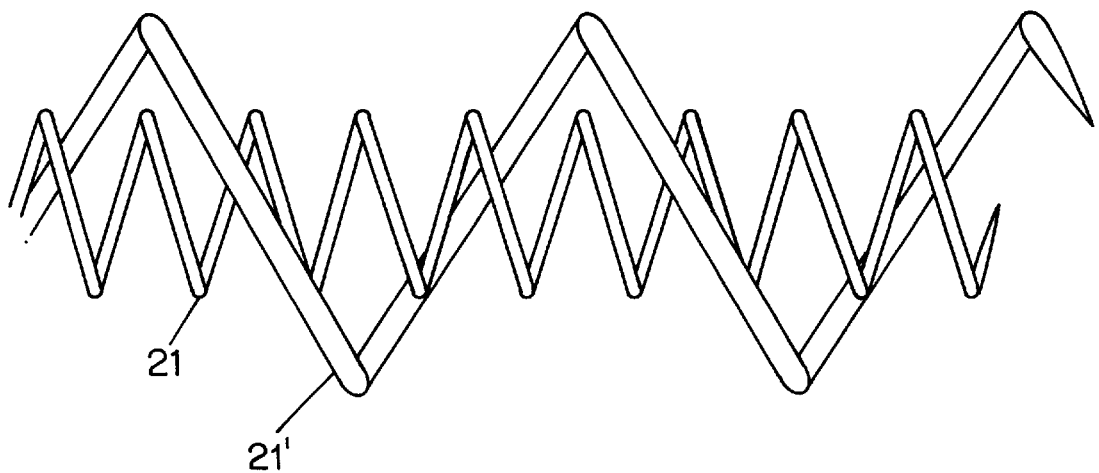

Another embodiment of the helical suture instrument comprises two helices 21, 21' (FIGS. 3A–3C). This device can be rotated and counter-rotated in a synchronized manner. The two helices 21, 21' are disposed side by side, with generally parallel central axes of rotation. By "side by side" is meant immediately next to each other, up to a set distance apart. When co-rotated, this device is used to place two separate but helically parallel sutures in an incision. Counter-rotation achieves a crossed suture pattern. The two helices may have the same central axis of rotation, or the two helices may be offset, with their central axes of rotation separated by a set distance.

The offset double helical member provides a method for placement of two intertwined sutures with separated but parallel central axis. This device can be used to close an incision that is too wide to close with a single helix. The concept can be extended to include more than two intertwined helixes that can be used for weaving several strands of sutures together. The offset double helical member consists of two helixes with identical diameters, turns, and pitches, which are intertwined but with parallel central axis separately by a preset distance. The operation is by one of two methods: a) co-rotating helixes typically synchronized by an intermediate gear between the gears on each side of the helix shaft, or b) counter-rotating helixes typically synchronized by gears on each helix shaft. The helixes must have opposite pitch directions: one is right-handed and the other is left-handed.

A variation consists of two co-rotating coaxial helical members, with one helix having a smaller radius to achieve the suture pattern shown in FIG. 3C. This concept can be extended to triple or even quadruple helices, or can be extended to double helices with independent variation in number of turns, pitch, radius, and diameter. The helix radius can be decreased or increased along the length of the helix for special applications. For example, a helical member with a radius decreasing from the straight portion to the sharpened tip may be used for wounds with decreasing diameter from the top to the bottom of the wound. In one embodiment, both of the helical members are solid, and have a catch or other means of attaching a suture near the tip of each helix. One method of using this type of suturing instrument is to use a single length of suture material with loops formed at the two free ends of the suture for attachment to the end of each helix. The double helical instrument is rotated into a tissue, and the loops of the suture are attached to the ends of the helices. When the double helical instrument is counter-rotated and withdrawn, it pulls both ends of the suture back through the helix tracts, and afterwards a single knot is tied for final closure. This method has the advantage of requiring only one knot to be tied in the suture.

Another component of the invention is a mechanism to drive or power the rotation and counter-rotation of the rigid helix. This may be accomplished by manual rotation of the helix via an attached handle and shaft, typically by a human operator or by using a motor capable of generating sufficient torque. A reversible electric motor may also be used. The mechanical advantage can be improved in manual systems by adding knobs, cranks, or ratchets.

The handle part of the helical suturing instrument has many variations. The handle is designed to allow manual or mechanical grip and application of torque to the shaft in order to rotate or counter-rotate the helix through tissue. Because every embodiment of the invention requires rotation followed by counter-rotation for each suture cycle, reversible direction of rotation is essential for the handle portion of the device. This can be achieved mechanically by a ratchet attached to the end of the straight portion of the helical member, or can be achieved by attachment of a reversible electric motor attached to the end of the straight portion. The electric motor can be designed to accept interchangeable helixes to increase its versatility.

Figure 9A:
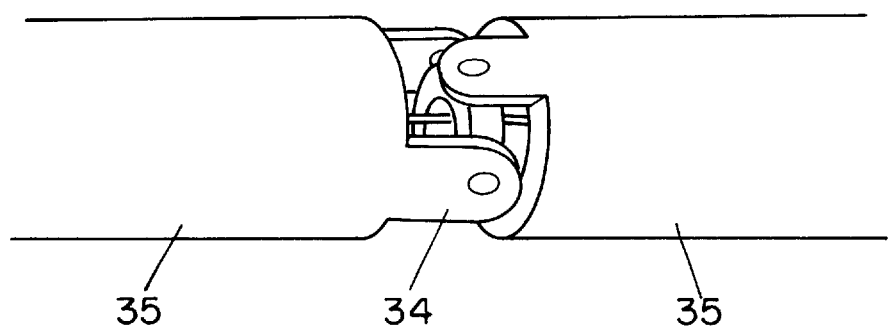
FIGS. 9A–9C show the universal joint on the handle of one embodiment.
Figure 9B:
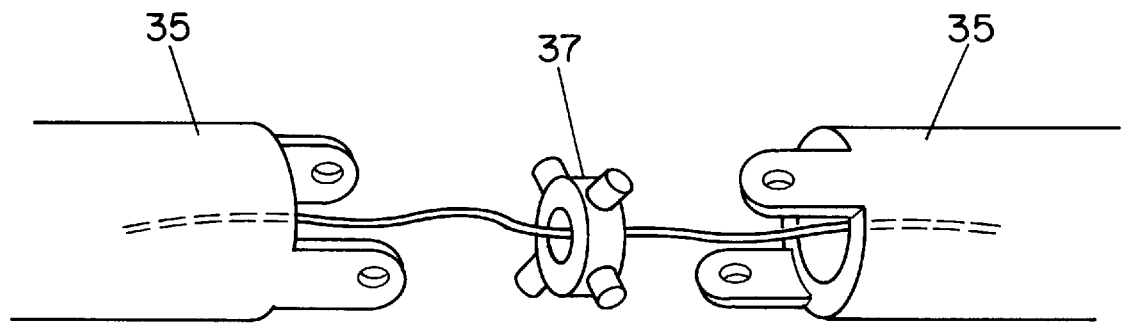
Figure 9C:
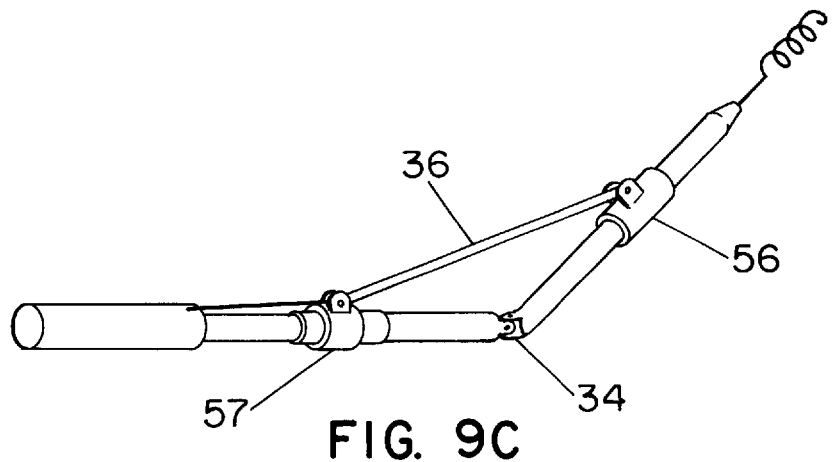

Another variation on the handle is a universal joint 34 (FIGS. 9A–9C), which allows the handle 35 to be bent at various angles to allow access to incisions with difficult positions relative to the operator. The universal joint allows greater control of the orientation of the helix to align longitudinally with an incision around corners or in a confined space. A movable diagonal brace 36 bridging each side of the universal joint 34 can be used for greater adjustment and control of the angle of the universal joint. This device is especially useful for endoscopic instruments because the direction of the trocar is usually different from the direction of the incision to be closed. A basic universal joint is sufficient for "pulling" type II devices, but because "pushing" type I devices require passage of a freely moving suture through a hollow member, the universal joint requires a "doughnut" or disk 37 cross member to attach the different sections of the handle.

The instant invention requires a rigid helical "needle" capable of controlled penetration of the substrate. Depending on substrate resistance, the helix should be made of an appropriately strong material. For instance, steel may be required to penetrate a tough leather substrate, but plastic or wood may be all that is required to penetrate tissue paper. Medical applications require a biologically inert material which is strong enough to penetrate tissue, but will not irritate living biological cells. Examples of such biologically inert materials are stainless steel and titanium. The greater the number of turns in the helix, the stronger the material required because tissue resistance increases as the surface area of contact with the substrate increases.

The helical needle can have variations in cross section shape, wall thickness, straight portion length, and in the attachment of the straight portion to the helical portion. For example, while the preferred cross-section shape is circular, square, hexagonal, or other shapes are also possible. The wall thickness will generally depend on the number of helical rotations and the diameter of the helix, and should be adjusted for the required strength needed for a particular application. Helical needles with large diameters and many helical rotations will need a thicker wall to prevent distortion of the helix as the needle is driven into the tissue.

The axis of the helix portion of the instrument is the central line running down the middle of the coils, one turn of the helix is the portion which completes a 360-degree rotation around the axis. The pitch of the helix is the angle of the body of the helix compared to a perpendicular to the axis (the steepness of the helix). The radius of the helix is the distance from the outer edge of the helix to the central axis. The diameter of the helical needle is the distance from one side of the member forming the helix to the other side (the thickness of the needle). Variations in the helix may be used for different applications. The radius of the helix can be changed to allow closure of incisions of various sizes and widths. The pitch of the helix can be changed to adjust the spacing of the sutures within the incision. The diameter of the member can be changed to accommodate requirements for helix strength or depth of suture placement. The number of turns can be adjusted to allow placement of a small number or large number of stitches with each stitch cycle.

Suturing applications require a wide range of stitch widths, total number of stitches, or density of stitches (number of stitches per inch). These requirements can be met by selecting a rigid helix with the appropriate helix diameter, needle thickness, pitch, and number of turns. Some applications that require a very large number of sutures or that involve a very resistant substrate may exceed the frictional resistance limit of the helix design. These applications can be broken up into smaller sections, with sutures placed sequentially in series.

For type I devices involving a hollow helix and detachable needle tip, a means for attaching the suture is required. The means for attaching a suture include any means by which the suture is held secure at or near the needle tip. Additionally, a means for maintaining tension on the internal suture during the rotation phase may be used to prevent the needle tip from detaching from the helix prematurely when it encounters resistance forces in the substrate. Suture tension can be achieved by holding the suture taut at the back end of the hollow helix with a snag or a spring clip.

The type I suture instrument is a hollow metal tube bent into a helix, with one end of the helix capped with a sharp needle point which is detachable from the helix proper. Because the needle point is subjected to substantial forces during rotation of the helix through tissue, it would prematurely detach from the end of the helix if it were not held in place by some method. The standard method to prevent this premature detachment would be maintenance of tension on the suture attached to the needle tip which passes through the interior of the hollow helix tube. With sufficient tension, the needle tip is pulled and held firmly in place on the end of the helix. Maintenance of suture tension is achieved by the suture holders illustrated here. The spring clip holder is a jaw-shaped device typically held in a closed position by spring tension. The suture snag device is a passive slot cut into a hard surface attached to the end of the helix, and the pivot gears are active devices that are held against each other by a spring. The suture can be inserted or removed from each of these holders as required for the suture cycle.

The above design requirements, customized to any particular application, can be achieved by mixing or matching different components of the invention. These components include the suture holder, handle, power driver, suture channel, shaft, helix transition, rigid helix proper, suture attachment mechanism, and needle point.

Figure 10A:
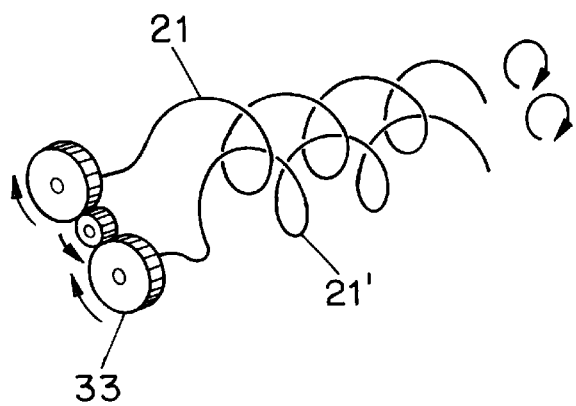
FIGS. 10A–10C show a co-rotating double helical member.
Figure 10B:
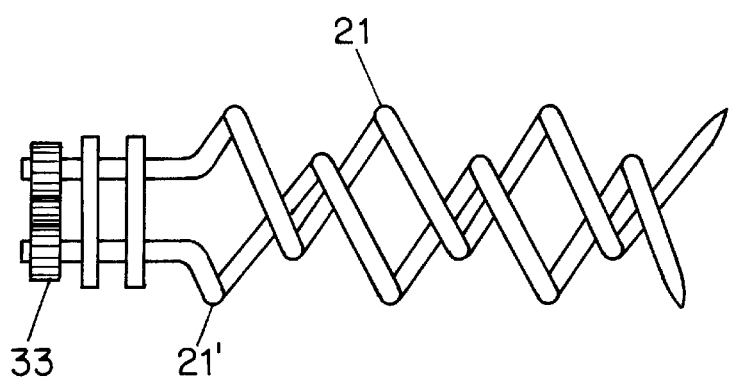
Figure 10C:
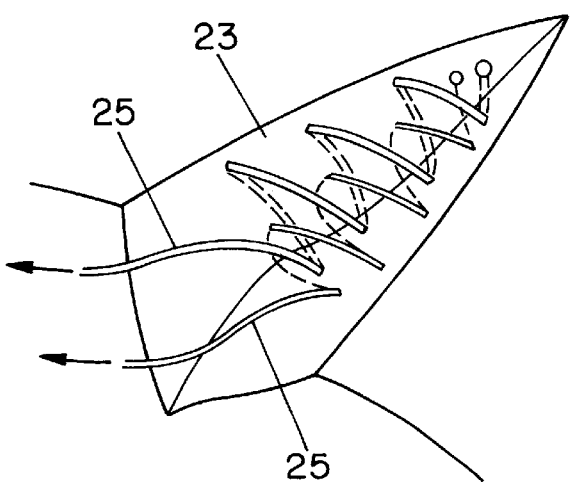

An offset embodiment of the double helical member instrument allows for closure of wide incisions (FIGS. 10A–10C). The offset double helical member suturing device comprises two helices 21, 21' attached to a connecting means 33. The connecting means facilitates the co-rotation of the two helical members. The two helices have parallel central axes separated from each other. Both helices co-rotate in the same direction, and have the same coil direction. They are interlocked so that the vertex of each helix turn is separated by one-half coil distance. In a preferred embodiment, the connecting means is a gear system which contains an intermediate center gear to allow for co-rotation. Both helices rotate together in the same direction at the same speed, and therefore will not collide. This allows placement of an offset double helical member suture pattern which is useful for increased strength or for closing a wide tissue gap.

An alternate embodiment is the offset counter-rotating double helical member. Counter-rotation is coordinated by a gear system at the end of each shaft with no intervening center gear. The bottom diagram is improperly drawn because opposite turn directions are not illustrated, but a model of this device made out of coiled solder wire functions well. Some applications require rotation and advance placement of the first helix, followed by rotation and advance of the second helix intertwined with the first, then reversing the order of helix motion during the counter-rotation and withdrawal step. This results in an opposite crossed suture pattern which can also be used to bridge over wide tissue gaps.

Alternative embodiments of the instant invention include a suture helix device containing a heating element on the tip which is used to penetrate thick or hardened material. The heating element melts through the material as the helix is rotated and advanced, and is used for suturing thick or strong material which has the proper melting properties. Another embodiment is a suture helix which contains an advancing tip consisting of a rotating drill bit. The conical drill bit can be powered by a spinning cable rotating freely within a hollow helix, or can be powered by a motor disposed just behind the drill tip inside the helix. This device is used to drill through hard or thick material during the rotation and advance step.

A number of different methods for placing, anchoring, applying tension, and tying or securing sutures using the helical suturing instrument can be used. Selection of the suturing strategy depends on the accessibility, size, and circumstances of the incision to be closed, along with specific application required.

A very basic Type I suture strategy involves extracting a suture from the tip of the helix and pulling the suture freely through the helix until enough length is available to return to the base of the helix. Once the Type I helix has been counter-rotated and withdrawn, a knot can be tied with the two free ends of the suture to close the incision. Another Type I suture strategy involves pulling the return suture freely through the coils of the suture helix along the axis of the helix before counter-rotation and withdrawal of the helical device. An end fitting disposed at the end of the suture anchors the far end of the suture in place. After the helix is counter-rotated and withdrawn, a sliding knot may be used to tighten and secure the near end of the suture. An example of a sliding knot is a disk with internal teeth which allows easy passage of suture in one direction, but high resistance to passage of this suture in the opposite direction. The sliding knot is pushed down the length of the near end of the suture to the incision, and the suture is pulled firmly through the sliding knot to close the incision. Once this is done, the suture will not travel backward through the sliding knot and will maintain closure tension on the incision.

In addition to the basic helix designs, other items can be incorporated into the invention to improve suturing function for specialized applications. These accessories include:

1. A light source disposed in the second open end of the straight hollow member to illuminate the working field and the needle end of the helical member. The light can be fiber optic from a remote light source or can consist of a light source powered at the end of the straight hollow member. The light is used to illuminate a difficult access or confined region to be sutured.

2. An optical channel in the straight hollow member containing an observation tool such as a fiber optic imaging system with a lens on the second end of the straight hollow member. This allows visualization of the suturing operation in a confined space. The imaging system may include a light source. The imaging system can be held in a stationary position with the helical mnenmber rotated around its axis, or the imaging system can be firmly attached to the helical member and is co-rotated with the helical member, requiring a counter-rotating camera or an electronic system to stabilize the image. This device can be used in a very confined region and allows the operator to continuously visualize the incision during the suturing steps.

3. Guide plates to allow suturing of exceptionally delicate or flimsy, or very tough substrates. The substrate material is compressed between two flat plates. Each flat plate has a series of evenly spaced holes drilled through it, which match the diameter and pitch of the helix. The plates are aligned adjacent to each other and the helical suturing instrument is then rotationally advanced through the holes. Slots cut from each hole to the edge of the plate are required to allow removal of the plates after the helical instrument has been withdrawn by counter-rotation. The most efficient slot pattern is diagonal cuts to match the pitch of the helix.

4. An instrument channel is a hollow straight member which does not extend all the way to the end of the helix. Various surgical or industrial instruments can then be placed through the channel to perform appropriate ancillary functions before, during or after placement of the helical suture. Examples of surgical instruments that can be used through an instrument channel include scissors, fluid aspiration cannula, fluid flush cannula, clamps, hooks, scalpels, suture loops, cauterization needles, or tissue holding corkscrews. Suture extractions from Type I helical devices or suture attachment to Type II helical devices can be performed by instruments passed through the instrument channel.

5. Trocars are larger diameter hollow cylinders used to initially penetrate tissue layers to create a hollow mechanical tract for placement of the helical suturing device. Straight cylindrical trocars are especially useful for outer helix diameters ranging from 3 to 12 mm. Helical trocars are especially useful for outer helix diameters ranging above 10–12 mm. Placement of the helical trocar is by torque rotation through the wall of the body cavity. This is facilitated by a sharp tip placed at the end of the trocar, and consisting of an internal solid helix which passes through the interior of the helical trocar. Once placement is completed, the internal solid pointed trocar core is counter-rotated out of the hollow helical trocar. The helical suture instrument can then be inserted and rotated through the interior of the helical trocar until it extends into the interior body cavity, and then can be directed to the internal incision to be closed. A double helical trocar is used to accommodate a double helical member suturing device.

6. Helix guides allow very accurate directional alignment and placement of the helical suturing device with its target substrate. Helix guide types include: a) freely mobile hollow cylindrical guides, b) extended handles attached to cylindrical guides, c) pivot handles, and d) internal helical grooves. Manipulation of the guide is used to control the position and placement of the helical suture instrument. The helix guide may be a generic cylinder, or it may have an extended handle for more accurate placement control. The interior of the cylindrical helix guide can be smooth, or can contain an internal helical groove matching the same dimensions as the helical instrument. The helical instrument is rotated through the interior of the cylindrical guide within the helical groove for even greater control. A remote method of controlling an endoscopic cylindrical helix guide involves manipulation rods passed through a trocar, then connected through pivoting hinges on an operator handle matching the pivoting hinges of the cylindrical helix guide.

After use, the Type I suture device can be reloaded with another suture so that the suture cycle can be repeated. Three basic suture reloading methods for Type I helical instruments include a) high-pressure gas or fluid, b) solid internal helical push rod, and c) magnetic or electromagnetic system. One embodiment of the high-pressure gas or fluid method involves pneumatic or hydraulic pressure applied at the base end of the hollow helix, which pushes an end fitting attached to a suture and sized to fit inside the helix along the entire length of the helix from base to tip, dragging the suture material behind it. Once the end fitting has been expelled from the tip end of the helix, the suture or its end fitting can be recovered and attached to the helix tip assembly. The pneumatic or hydraulic pressure method of suture reloading can be applied in either direction through the helix, from base to tip, or from tip to base.

A solid internal helical push rod may be used to push the end fitting attached to a suture through the hollow helical member. The suture is dragged behind the end fitting during this process; inserted into the base and expelled through the tip end. Once the end fitting and suture are expelled, the solid internal helical push rod is counter-rotated out of the hollow helical member.

The electromagnetic method of reloading suture into a Type I helix requires a nonmagnetic suture and an iron or magnetic end fitting. The end fitting with attached suture is inserted into the helical member. In one embodiment, a powerful electromagnet is then placed under the magnetic end fitting, and the helical member is rotated over the surface of the electromagnet. The electromagnet holds the magnetic end fitting in place, and the helical member is rotated underneath the magnetic end fitting until the tip of the helical member is reached. At this point, the magnetic end fitting is extracted from the tip of the helical member along with the suture, and the electromagnet is turned off. In an alternate embodiment, the electromagnet is moved over the helical member, dragging the magnetic end fitting through the helix from one end to the other.

An alternative to the reloading methods is to use relatively inexpensive materials for the helical suturing device, so that the device can be discarded after a single use.

I claim:

1. A suturing instrument comprising first and second members, the first member comprising a helical portion and a straight portion, the helical portion having a configuration including at least one complete revolution of a helix and having a sharpened tip, the helix having a central axis;

wherein the first member comprises a means for attaching a suture;

the second member comprising a straight hollow member having an interior lumen extending from a first open end to a second open end, wherein the straight portion of the first member is attached to the first end of the second member such that the second member is disposed within the helical portion of the first member along the central axis of the helix, the second end of the second member extending toward the sharpened tip of the first member.

2. The instrument of claim 1, wherein the first member is hollow, the helix has inner and outer curves, and the means for attaching a suture comprises a hinged opening in the outer curve of the helix;

wherein the instrument further comprises a length of suture material which is attached to an end fitting;

wherein the end fitting is positioned proximal to the hinged opening.

3. The instrument of claim 1, wherein the helix has inner and outer curves;

wherein at least part of the helical portion of the first member is hollow and comprises an internal space with an opening in the inner or outer curve of the helix;

wherein the means for attaching a suture comprises a suture bolder positioned inside the hollow part of the member, the suture holder comprising an extended length of suture material.

4. The instrument of claim 1, wherein the first member is hollow and the means for attaching a suture comprises a detachable sharpened tip;

the instrument further comprising a length of suture material, wherein the suture material is attached to the detachable sharpened tip and extends through the hollow member and exits from the straight portion.

5. The instrument of claim 4, wherein the detachable sharpened tip is hinged;

wherein the suture material is attached to an end fitting positioned inside the hollow first member such that the end fitting is located immediately inside the hinged sharpened tip and the length of suture extends through the hollow member and exits from the straight portion.

6. The instrument of claim 5, wherein the helix has inner and outer curves and the sharpened tip is hinged on the inner curve of the helix.

7. The instrument of claim 4, wherein the helix has inner and outer curves, the instrument further comprising an aperture in the inner curve of the helix near the sharpened tip, the aperture covered by a rupturable membrane;

the instrument further comprising a length of suture attached to an end fitting positioned inside the first hollow member such that the end fitting is located inside the aperture and the length of suture extends through the hollow member and exits from the straight portion.

8. The instrument of claim 4, wherein the sharpened tip comprises a break-away sharp tip and an expandable section at the end opposite the break-away sharp tip, and the suture is permanently attached to the expandable section such that when the sharpened tip is detached from the helical device, the expandable section expands to form an anchor.

9. The instrument of claim 1, wherein the sharpened tip comprises a freely detachable sharp tip;

the instrument further comprising a detachable end fitting, the end fitting being permanently attached to the suture;

the instrument further comprising a means for holding the suture located on the straight portion of the first member;

wherein the means for holding the suture maintains tension on the suture to hold the suture and detachable sharpened tip in place on the first member.

10. The instrument of claim 9, wherein the freely detachable sharp tip comprises external threads on the end opposite the sharp tip, wherein the first hollow member contains matching internal threads such that the sharp tip is screwed onto the first hollow member.

11. The instrument of claim 9, wherein the freely detachable sharp tip comprises internal threads on the end opposite the sharp tip, wherein the first hollow member contains matching external threads such that the sharp tip is screwed onto the first hollow member.

12. The instrument of claim 9, wherein the end fitting comprises an anchor;

the anchor functioning to secure the suture.

13. The instrument of claim 12, wherein the anchor is a toggle;

wherein in use, once the sharp tip is separated from the toggle the toggle is moved perpendicular to the suture, forming an anchor when the suture is pulled tight.

14. The instrument of claim 1, wherein the first member is solid and the means for attaching a suture is proximal to the sharpened tip.

15. The instrument of claim 14, wherein the first member further comprises a groove running the length of the member from the sharpened tip along the helical portion and the straight portion, the groove sized to hold a suture.

16. The instrument of claim 14, wherein means for attaching a suture is a catch located on the first member proximal to the sharpened tip.

17. The instrument of claim 16, further comprising a suture with a loop at one end, wherein in use, the loop of the suture is attached to the catch.

18. The instrument of claim 16, wherein the catch is a spring-mounted gate in the helix.

19. The instrument of claim 16, wherein the first open end of the second member comprises a hinged cover;

the instrument further comprising a length of suture material with a loop at one end, the suture material positioned inside the second member such that the loop end is proximal to the first end of the member.

20. The instrument of claim 16, wherein the catch is a notch in the helix.

21. The instrument of claim 1 further comprising a light source disposed in the first end of the second member.

22. The instrument of claim 1 further comprising an observation tool disposed in the first end of the second member.

23. The instrument of claim 1, further comprising a tether line attached to the second end of the second member.

24. The instnnnent of claim 1, further comprising a third member, the third member comprising a helical portion and a straight portion, the helical portion having a configuration including at least one complete revolution of a helix and having a sharpened tip, the helix having a central axis;

wherein the third member comprises a means for attaching a suture;

wherein the straight portion of the third member is attached to the first end of the second member such that the second member is disposed within the helical portions of the first and third members along the central axes of the helices, the second end of the second member extending toward but not beyond the sharpened tips of the first and third members.

25. The instrument of claim 24, wherein the helical portions of the first and third members have first and second radii and pitches, respectively, and wherein the radius and pitch of the first helix are different than the radius and pitch of the second helix.

26. The instrument of claim 24, wherein the first and third members are hollow and the means for attaching a suture comprises a detachable sharpened tip;

the instrument further comprising two lengths of suture material, wherein one length of suture material is attached to each detachable sharpened tip, the lengths of suture material extending through the first and third hollow members and exiting from the straight portions of the hollow members.

27. The instrument of claim 26, wherein the detachable sharpened tips are freely detachable and the instrument further comprises means for holding the suture located on the straight portions of the first and third members;

wherein the means for holding the suture maintains tension on the sutures to hold the sutures and detachable sharpened tips in place on the first and third members.

28. The instrument of claim 24 wherein the first and third members are solid and a means for attaching a suture is proximal to the sharpened tip of each of the first and third members.

29. The instrument of claim 28, wherein the means for attaching a suture is a catch located on the first and third members proximal to the sharpened tip.

30. The instrument of claim 29, wherein the first open end of the second member comprises a hinged cover;

the instrument ether comprising two lengths of suture material each with a loop at one end, the two lengths of suture material positioned inside the second member such that the loop ends are proximal to the first end of the second member.

31. The instrument of claim 24, further comprising a light source disposed in the first end of the second member.

32. The instrument of claim 24, further comprising an observation tool disposed in the first end of the second member.

33. The instrument of claim 24 further comprising a tether line attached to the second end of the second member.

34. The instrument of claim 24, wherein the first member is hollow and the means for attaching a suture comprises a detachable sharpened tip;

the instrument further comprising a length of suture material, wherein the suture material is attached to the detachable sharpened tip, the length of suture material extending through the first hollow member and exiting from the straight portion of the first hollow member;

wherein the third member is solid and the means for attaching a suture is proximal to the sharpened tip of the third member.

35. A suturing instrument comprising first and second members and a connecting member, the first and second members each comprising a helical portion and a straight portion, the helical portions each having a configuration including at least one complete revolution of a helix and having a sharpened tip, the helices each having a central axis;

wherein the first and second members each comprise a means for attaching a suture;

wherein the straight portions of the first and second members are attached to the connecting member such that the first and second members are disposed side by side, with parallel central axes.

36. The instrument of claim 35, wherein the first and second members have identical diameters and pitches;

wherein the first and second members are attached to the connecting member such that they are intertwined and have parallel central axes separated by a preset distance, such that the first and second members are offset.

37. The instrument of claim 36, wherein the first and second members have identical number of turns.

38. The instrument of claim 35, wherein the parallel central axes of the first and second members are identical.

39. The instrument of claim 35, wherein the first and second members have first and second helices having first and second radii and pitches, respectively, and wherein the radius and pitch of the first helix are different than the radius and pitch of the second helix.

40. The instrument of claim 35, wherein the first and second members are hollow and the means for attaching a suture comprises a detachable sharpened tip on each of the first and second members;

the instrument further comprising two lengths of suture material, wherein one length of suture material is attached to each detachable sharpened tip, the lengths of suture material extending through the first and second hollow members and exiting from the straight portions of the hollow members.

41. The instrument of claim 40, wherein the detachable sharpened tips are freely detachable and the instrument further comprises means for holding the suture located on the straight portions of the first and second members;

wherein the means for holding the suture maintains tension on the sutures to hold the sutures and detachable sharpened tips in place on the first and second members.

42. The instrument of claim 35, wherein the first and second members are solid and a means for attaching a suture is proximal to the sharpened tip of each of the first and second members.

43. The instrument of claim 42, wherein the means for attaching a suture is a catch located on the first and second members proximal to the sharpened tip.

44. The instrument of claim 35, wherein the first member is hollow and the means for attaching a suture comprises a detachable sharpened tip;

the instrument further comprising a length of suture material, wherein the suture material is attached to the detachable sharpened tip, the length of suture material extending through the first hollow member and exiting from the straight portion of the first hollow member;

wherein the second member is solid and the means for attaching a suture is proximal to the sharpened tip of the second member.

45. A suturing instrument comprising at least a first member and a handle, the member having a helical portion and a straight portion, the helical portion having a configuration including at least one complete revolution of a helix and having a sharpened tip, the helix having a central axis;

wherein the member comprises a means for attaching a suture;

the handle comprising first and second sections connected by a universal joint;

wherein the handle is attached to the straight portion of the member.

46. The instrument of claim 45, further comprising an adjustable bracket attached at a first end to the first section of handle and attached at a second end to the second section of handle;

wherein the adjustable bracelet comprises a sliding adjustment means which allows the first and second sections of the handle to be placed into a desired position with any angle between the first and second sections of handle, the adjustable bracket then securing the first and second sections of the handle to keep the instrument in the desired position.

47. The instrument of claim 45, wherein the member and first and second handle sections are hollow and each has an interior lumen extending from a first open end to a second open end;

wherein the lumens of the member and first and second handle sections are aligned;

wherein the means for attaching a suture comprises a detachable sharpened tip;

the instrument further comprising a length of suture material, wherein the suture material is attached to the detachable sharpened tip and extends through the hollow member and first and second handle sections and exits from the second open end of the second handle section;

wherein the universal joint comprises a ring with an inner hollow bore, the ring positioned between the first and second handle portions such that the hollow bore of the ring is aligned with the lumens of the first and second handle sections, allowing the suture to travel freely through the hollow member from the sharpened tip through the handle.

48. The instrument of claim 45, further comprising a second member, the second member comprising a helical portion and a straight portion the helical portion having a configuration including at least one complete revolution of a helix and having a sharpened tip, the helix having a central axis;

wherein the second member comprises a means for attaching a suture;

wherein the straight portion of the second member is attached to the handle such that the first and second members are side by side.

49. A suturing instrument comprising first and second members and means for simultaneously rotating the first and second members;

the first and second members each comprising a helical portion and a straight portion, the helical portion having a configuration including at least one complete revolution of a helix and having a sharpened tip, the helix having a central axis, the first and second members each comprising a means for attaching a suture;

wherein the straight portions of the first and second members are attached to the means for simultaneously rotating the first and second members.

50. The instrument of claim 49, wherein the first and second members have identical diameters, number of turns, and pitches;

wherein the first and second members are intertwined and have parallel central axes separately by a preset distance such that the first and second members are off-set.

51. The instrument of claim 49, wherein the means for rotating comprises means for co-rotating the first and second members.

52. The instrument of claim 49, wherein the means for rotating comprises means for counter-rotating the first and second members.

53. A method for suturing a tissue comprising introducing a suturing instrument into the tissue, wherein the instrument comprises first and second members the first member comprising a helical portion and a straight portion, the helical portion having a configuration including at least one complete revolution of a helix and having a sharpened tip, the helix having a central axis;

wherein the first member comprises a means for attaching a suture;

wherein the instrument further comprises a suture, wherein the suture is attached to the sharpened tip;

the second member comprising a straight hollow member having an interior lumen extending from a first open end to a second open end, wherein the straight portion of the first member is attached to the first end of the second member such that the second member is disposed within the helical portion of the first member along the central axis of the helix, the second end of the second member extending toward but not beyond the sharpened tip of the first member;

rotating the instrument in a first direction into the tissue, creating a path for the suture;

rotating the instrument in a second direction out of the tissue;

wherein the suture is deposited along the path.

54. The method of claim 53, further comprising the step of observing the suturing process via an observation tool disposed in the first end of the second member.

55. The method of claim 53 wherein the first member is hollow and the means for attaching a suture comprises a detachable sharpened tip;

wherein the suture material is attached to the detachable sharpened tip and extends through the hollow member and exits from the straight portion of the first member;

wherein after rotating the instrument into the tissue, the detachable sharpened tip is removed and the attached suture is held in place while the instrument is rotated out of the tissue.

56. The method of claim 53, wherein the first member is solid and the means for attaching a suture is a catch proximal to the sharpened tip;

wherein after the instrument has been rotated into the tissue, a suture is attached to the catch and when the instrument is rotated out of the tissue, the suture is deposited along the path of the instrument.

57. The method of claim 53, wherein the helix has inner and outer curves;

wherein at least part of the helical portion of the first member is hollow and comprises an internal space with an opening in the inner or outer curve of the helix;

wherein the instrument further comprises a suture holder positioned inside the hollow part of the member, the suture holder comprising an extended length of suture material;

wherein after the instrument is rotated into the tissue, the method further comprises the steps of removing a length of suture from the suture holder through the opening and holding the suture as the instrument is rotated out of the tissue;

wherein the extended length of suture is deposited along the path.

58. The method of claim 53 wherein the instrument further comprises a tether line attached to the second end of the second member, and the step of rotating the instrument in a first direction into the tissue further comprises manipulating the tether line to guide and position the instrument into the tissue.

59. A method for loading a suture into a helical suturing instrument, the suturing instrument comprising at least a first hollow member having an interior lumen extending from a first open end to a second open end, the member having a helical portion and a straight portion, the helical portion having a configuration including at least one complete revolution of a helix and having a detachable sharpened tip;

the method comprising attaching a length of suture material to an end fitting, placing the end fitting with attached suture into one end of the hollow member, and moving the end fitting through the hollow member from one end to the other end, wherein the end fitting deposits the suture material along the length of the hollow member.

60. The method of claim 59, wherein the step of moving the end fitting through the hollow member is achieved by forcing gas or fluid into the hollow member.

61. The method of claim 59, wherein the step of moving the end fitting through the hollow member is achieved by inserting an internal helical push rod into the hollow member behind the end fitting and pushing the end fitting and attached suture material through the hollow member;

wherein the internal helical push rod has a shape and size to fit inside the hollow member.

62. The method of claim 59, wherein the end fitting is magnetic and wherein the step of moving the end fitting through the hollow member is achieved by moving a magnet along the member from one end to the other end.

* * * * *

UNITED STATES PATENT AND TRADEMARK OFFICE
CERTIFICATE OF CORRECTION

PATENT NO. : 6,626,917 B1
DATED : September 30, 2003
INVENTOR(S) : Craig

It is certified that error appears in the above-identified patent and that said Letters Patent is hereby corrected as shown below:

<u>Title page,</u>
Please add the following Items:
-- [60]  Related U.S. Application Data Provisional Application No. 60/161,584, filed on 10/26/1999 --
-- [74]  *Attorney, Agent or Firm*, Oppedahl & Larson LLP --

<u>Column 7,</u>
Line 32, change "entirety" to -- entirely --

<u>Column 14,</u>
Line 45, change "mnenmber" to -- member --

<u>Column 16,</u>
Line 65, change "bolder" to -- holder --

<u>Column 18,</u>
Lines 7 through 16, delete claims 18, 19 and 20, and insert the following claims:
-- 18. The instrument of claim 16, wherein the catch is a notch in the helix
   19. The instrument of claim 16, wherein the catch is a spring-mounted gate in the helix
   20. The instrument of claim 16, wherein the first open end of the second member comprises a hinged cover; the instrument further comprising a length of suture material positioned inside the second member such that the loop end is proximal to the first end of the member. --
Line 24, change "instnnnent" to -- instrument --
Line 25, change the second "member" to -- device --
Line 66, change "ether" to -- further --

UNITED STATES PATENT AND TRADEMARK OFFICE
CERTIFICATE OF CORRECTION

PATENT NO. : 6,626,917 B1
DATED : September 30, 2003
INVENTOR(S) : Craig

It is certified that error appears in the above-identified patent and that said Letters Patent is hereby corrected as shown below:

Column 20,
Line 34, change "bracelet" to -- bracket --

Signed and Sealed this

First Day of June, 2004

JON W. DUDAS
*Acting Director of the United States Patent and Trademark Office*